(12) United States Patent
Li (10) Patent No.: US 9,436,889 B2
(45) Date of Patent: Sep. 6, 2016

(54) IMAGE PROCESSING DEVICE, METHOD, AND PROGRAM

(71) Applicant: FUJIFILM Corporation, Tokyo (JP)

(72) Inventor: Yuanzhong Li, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/668,196

(22) Filed: Mar. 25, 2015

(65) Prior Publication Data

US 2015/0199586 A1    Jul. 16, 2015

Related U.S. Application Data

(63) Continuation of application No. PCT/JP2013/005751, filed on Sep. 27, 2013.

(30) Foreign Application Priority Data

Sep. 28, 2012  (JP) ................................ 2012-217935

(51) Int. Cl.
*G06K 9/00* (2006.01)
*G06K 9/46* (2006.01)
(Continued)

(52) U.S. Cl.
CPC ........... *G06K 9/4604* (2013.01); *A61B 5/0037* (2013.01); *A61B 5/055* (2013.01); *A61B 5/489* (2013.01); *A61B 5/7485* (2013.01); *A61B 6/032* (2013.01); *A61B 6/037* (2013.01); *A61B 6/12* (2013.01); *A61B 8/085* (2013.01); *G06K 9/4642* (2013.01); *G06T 7/0081* (2013.01); *G06T 7/0093* (2013.01); *G06T 7/602* (2013.01); *A61B 5/08* (2013.01); *G06T 2207/10004* (2013.01); *G06T 2207/10081* (2013.01);
(Continued)

(58) Field of Classification Search
None
See application file for complete search history.

(56) References Cited

U.S. PATENT DOCUMENTS

2008/0044080 A1*  2/2008 Li ............................ G06K 9/34
                                                    382/155
2009/0310883 A1   12/2009 Moriya
2012/0230583 A1    9/2012 Inoshita

FOREIGN PATENT DOCUMENTS

JP     2002-008045 A    1/2002
JP     2007-159934 A    6/2007
(Continued)

OTHER PUBLICATIONS

Patrick Therasse et al., "New Guidelines to Evaluate the Response to Treatment in Solid Tumors", Journal of the National Cancer Institute, Feb. 2, 2000, pp. 205-216, vol. 92, No. 3.
(Continued)

*Primary Examiner* — Hadi Akhavannik
(74) *Attorney, Agent, or Firm* — Sughrue Mion, PLLC (57) ABSTRACT

A region setting unit and a specific region extracting unit are included. The region setting unit sets, within an input image that is photographed at a reference time point out a first region estimated as highly probable to be a specific region and a second region estimated as highly probable to be a background region, which is a region other than the specific region. The specific region extracting unit extracts the specific region within the input image based on a first histogram which is a histogram of density values in the first region and a second histogram which is a histogram of density values in the second region. The specific region extracting unit extracts a specific region from the input image that is photographed at a time point different from the reference time point, based on the first histogram and the second histogram.

18 Claims, 7 Drawing Sheets

(51) Int. Cl.
*G06T 7/00* (2006.01)
*G06T 7/60* (2006.01)
*A61B 5/055* (2006.01)
*A61B 6/03* (2006.01)
*A61B 6/12* (2006.01)
*A61B 8/08* (2006.01)
*A61B 5/00* (2006.01)
*A61B 5/08* (2006.01)

(52) U.S. Cl.
CPC ............... *G06T 2207/20148* (2013.01); *G06T 2207/30096* (2013.01); *G06T 2207/30101* (2013.01)

(56) References Cited

FOREIGN PATENT DOCUMENTS

JP          2009-301254 A       12/2009
WO         2011/061905 A1       5/2011

OTHER PUBLICATIONS

Yu Masuda et al., "CT Image Contrast Enhancement and Liver Tumor Detection by using Probability Density Functions and EM/MPM Algorithms (MR/AR no Jitsuyoka ni Muketa CV/PR Gijutsu no Kadai to Tenbo.)", IEICE Technical Report, PRMU, Pattern Ninshiki Media Rikai, 2011, pp. 21-26, vol. 110, No. 381.
Yuri Y. Boykov et al., "Interactive Graph Cuts for Optimal Boundary & Region Segmentation of Objects in N-D Images", Computer Vision, ICCV, Proceedings, Eighth IEEE International Conference on, 2001, pp. 105-112, vol. 1.
International Search Report of PCT/JP2013/005751 dated Dec. 17, 2013 English.
Communication dated Oct. 20, 2015 from the Japanese Patent Office issued in corresponding Japanese Application No. 2012-217935.

* cited by examiner

INPUT IMAGE I1 OF REFERENCE TIME POINT

INPUT IMAGE I2 OF TIME POINT DIFFERENT
FROM REFERENCE TIME POINT

RA3

IMAGE PROCESSING DEVICE, METHOD, AND PROGRAM

CROSS REFERENCE TO RELATED APPLICATIONS

The present application is a Continuation of PCT International Application No. PCT/JP2013/005751 filed on Sep. 27, 2013, which claims priority under 35 U.S.C. §119(a) to Japanese Patent Application No. 2012-217935 filed on Sep. 28, 2012. Each of the above applications is hereby expressly incorporated by reference in its entirety, into the present application.

BACKGROUND OF THE INVENTION

1. Technical Field

The present invention relates to an image processing device, method, and program for extracting a specific region based on the density values of pixels within an input image.

2. Background Art

In the medical field, measuring changes in tumor mass is an important element for clinical evaluation of a cure for cancer, and an objective tumor reducing effect and exacerbation of the original disease have both been used as important endpoints in clinical tests for cancer.

In P. Therasse et al., "New Guidelines to Evaluate the Response to Treatment in Solid Tumors", Journal of the National Cancer Institute, Vol. 92, No. 3, pp. 205-216, 2000 (Non Patent Literature 1), for example, it is proposed to use the longest diameter of a tumor region and the longest distance in a direction orthogonal to the longest diameter as indices for evaluating the exacerbation of a tumor or the tumor curing effect.

However, this simple measuring of the longest diameter of a tumor region and the longest distance in a direction orthogonal to the longest diameter yields rough measurements of the tumor, not precise area and volume measurements of the tumor.

In another proposal that has been made, a specific region such as a tumor region or a blood vessel region is extracted from a three-dimensional image photographed by a computed tomography (CT) machine or other modalities, and is displayed to be used for medical diagnostic imaging.

A possible way to check the tumor curing effect or the exacerbation of a tumor as described above is, for example, a method in which three-dimensional images of the same patient that are photographed at different points in time are acquired and tumor regions respectively extracted from those three-dimensional images are displayed.

In Japanese Unexamined Patent Publication No. 2009-301254 (Patent Literature 1), for example, there is proposed a method in which three-dimensional images are photographed at different points in time, a first shadow region is detected in one of the three-dimensional images that is photographed at a given point in time, and position information of a given point in the first shadow region is used to extract a second shadow region corresponding to the first shadow region from another of the three-dimensional images that is photographed at another point in time.

DISCLOSURE OF THE INVENTION

However, when extracting tumor regions respectively from three-dimensional images that are photographed at different points in time as described above, corresponding tumor regions cannot be extracted accurately by using different standards of extraction.

For instance, an exact change in tumor region size cannot be grasped if, whereas a region containing a portion where the symptom is not so severe is extracted as a tumor region from a three-dimensional image that is photographed at a given point in time, a portion where the symptom has progressed far and the density and the like have clearly changed is extracted as a tumor region from a three-dimensional image that is photographed at another point in time.

In view of this circumstance, it is an object of the present invention to provide an image processing device, method, and program which are capable of extracting, when specific regions such as tumor regions are to be extracted respectively from images photographed at different points in time as described above, the specific regions with the use of the same standard.

An image processing device according to one embodiment of the present invention includes: an image acquiring unit for acquiring a plurality of input images of the same subject photographed at different points in time; a region setting unit for setting, within an input image that is photographed at a reference time point out of the plurality of input images acquired by the image acquiring unit, a first region estimated as highly probable to be a specific region and a second region estimated as highly probable to be a background region, which is a region other than the specific region; and a specific region extracting unit for calculating a first histogram, which is a density histogram of respective density values of pixels in the first region, and a second histogram, which is a density histogram of respective density values of pixels in the second region, and extracting the specific region within the input image that is photographed at the reference time point, based on the first histogram and the second histogram, in which, based on the first histogram and the second histogram which are calculated with use of the input image photographed at the reference time point, the specific region extracting unit extracts a specific region corresponding to the specific region within the input image that is photographed at the reference time point from one of the plurality of input images that is photographed at a time point different from the reference time point.

Further, in the image processing device according to one embodiment of the present invention, the specific region extracting unit may be configured to: calculate, for each density value, based on the first histogram and the second histogram, a first evaluation value which indicates a likelihood that the density value represents the specific region; calculate, for every two adjacent pixels within the input image, a second evaluation value which indicates a likelihood that the two adjacent pixels represent an outline, based on the respective first evaluation values of the density values of the two adjacent pixels; and define a first reference vertex which belongs to the specific region, a second reference vertex which belongs to the background region, and a plurality of vertices respectively representing the pixels within the input image, set a connection cost, which indicates how likely the plurality of vertices are to be connected to each other, based on the second evaluation value, and connect the vertices to each other based on the set connection cost, thereby extracting the specific region.

The meaning of "two adjacent pixels" in the above encompasses not only two pixels that are directly next to each other but also two pixels the distance between which is so short relative to the size of the input image that the pixels can be deemed as adjacent to each other.

The phrase "set a connection cost, which indicates how likely the respective vertices are to be connected to each other, based on the second evaluation value" in the above means that at least some connection costs selected from the group consisting of a connection cost that indicates how likely the first reference vertex is to be connected to the vertices that represent pixels, a connection cost that indicates how likely the second reference vertex is to be connected to the vertices that represent pixels, and a connection cost that indicates how likely the plurality of vertices that represent the plurality of pixels are to be connected to each other, are set based on the second evaluation value.

Further, the specific region extracting unit may calculate the first evaluation value based on a ratio of a frequency value in the first histogram and a frequency value in the second histogram.

Further, the specific region extracting unit may calculate the first evaluation value based on a difference between a frequency value in the first histogram and a frequency value in the second histogram.

Further, the specific region extracting unit may calculate, for each pixel within the input image, the second evaluation value so that the likelihood that the two adjacent pixels represent an outline becomes higher as a difference between the first evaluation values of the two adjacent pixels becomes larger.

Further, based on the second evaluation value, the specific region extracting unit may set the connection cost so that the vertices corresponding to the two adjacent pixels become less likely to be connected to each other as the likelihood that the two adjacent pixels represent an outline becomes higher.

Further, the image processing device may further include a long diameter setting unit for setting a long diameter of the specific region within the input image that is photographed at the reference time point, and the region setting unit may set the first region and the second region based on the long diameter received by the long diameter setting unit.

It is sufficient if "the long diameter of a specific region" in the above is a length deemed as indicative of an approximate long diameter of the specific region. For example, in the case where the "long diameter of a specific region" in the above is one based on information set and input by a user which is determined by the user on an input image as the long diameter of a specific region, the diameter does not need to strictly match the longest diameter of the specific region.

Further, the image processing device may further include a long diameter setting unit for setting a long diameter of the specific region within the input image that is photographed at the reference time point, and the specific region extracting unit may set the connection cost so that the vertices that are within a given range from the long diameter are more likely to be connected to the first reference vertex.

Further, the image processing device may further include a long diameter setting unit for setting a long diameter of the specific region within the input image that is photographed at the reference time point, and the specific region extracting unit may set the connection cost so that the vertices that correspond to pixels located outside two ends of the long diameter in a direction in which the long diameter extends are more likely to be connected to the second reference vertex.

"Set" the connection cost of connecting the vertices to each other "so that the vertices are more likely to be connected" means that the connection cost is set to be relatively high in the case where an evaluation function used by the specific region extracting unit is a type that gives a higher evaluation for the likelihood of connection as the connection cost becomes higher, and means that the connection cost is set to be relatively low in the case where the evaluation function used by the specific region extracting unit is a type that gives a lower evaluation for the likelihood of connection as the connection cost becomes higher. "Set" the connection cost "so that the vertices are less likely to be connected" means that the connection cost is set to be relatively low in the case where the evaluation function used by the specific region extracting unit is a type that gives a higher evaluation for the likelihood of connection as the connection cost becomes higher, and means that the connection cost is set to be relatively high in the case where the evaluation function used by the specific region extracting unit is a type that gives a lower evaluation for the likelihood of connection as the connection cost becomes higher.

Further, the region setting unit may set, as the first region, a region contained in an elliptical region that has the long diameter as its major axis.

Further, the region setting unit may set, as the second region, a region of a given shape that is located outside a circle whose diameter is the long diameter.

Further, the specific region may be a tumor region or a blood vessel region.

An image processing method according to one embodiment of the present invention includes: acquiring a plurality of input images of the same subject photographed at different points in time; setting, within an input image that is photographed at a reference time point out of the plurality of acquired input images, a first region estimated as highly probable to be a specific region and a second region estimated as highly probable to be a background region, which is a region other than the specific region; calculating a first histogram, which is a density histogram of respective density values of pixels in the first region, and a second histogram, which is a density histogram of respective density values of pixels in the second region, and extracting the specific region within the input image that is photographed at the reference time point, based on the first histogram and the second histogram; and extracting, based on the first histogram and the second histogram which are calculated with use of the input image photographed at the reference time point, a specific region corresponding to the specific region within the input image that is photographed at the reference time point from one of the plurality of input images that is photographed at a time point different from the reference time point.

An image processing program according to one embodiment of the present invention causes a computer to execute the procedures of: acquiring a plurality of input images of the same subject photographed at different points in time; setting, within an input image that is photographed at a reference time point out of the plurality of acquired input images, a first region estimated as highly probable to be a specific region and a second region estimated as highly probable to be a background region, which is a region other than the specific region; calculating a first histogram, which is a density histogram of respective density values of pixels in the first region, and a second histogram, which is a density histogram of respective density values of pixels in the second region, and extracting the specific region within the input image that is photographed at the reference time point, based on the first histogram and the second histogram; and extracting, based on the first histogram and the second histogram which are calculated with use of the input image photographed at the reference time point, a specific region corresponding to the specific region within the input image that is photographed at the reference time point from one of the plurality of input images that is photographed at a time point different from the reference time point.

According to the image processing device, method, and program of the one embodiment of the present invention, within an input image that is photographed at a reference time point out of a plurality of input images of the same subject photographed at different points in time, a first region estimated as highly probable to be a specific region and a second region estimated as highly probable to be a background region, which is a region other than the specific region, are set. A first histogram which is a density histogram in the first region and a second histogram which is a density histogram in the second region are calculated. The specific region within the input image that is photographed at the reference time point is extracted based on the first histogram and the second histogram, and a specific region corresponding to the specific region within the input image that is photographed at the reference time point is extracted, based on the first histogram and the second histogram, from one of the input images that is photographed at a time point different from the reference time point. The specific regions can thus be extracted with the use of the same standard from the input image that is photographed at the reference time point and from an input image that is photographed at a time point different from the reference time point, by using the first histogram and the second histogram in both cases.

Consequently, in the case of extracting, for example, a tumor region as a specific region, portions where the symptom has progressed to approximately the same degree can respectively be extracted as tumor regions, and an exact change in size between those regions can be grasped.

BEST MODE FOR CARRYING OUT THE INVENTION

Figure 1:
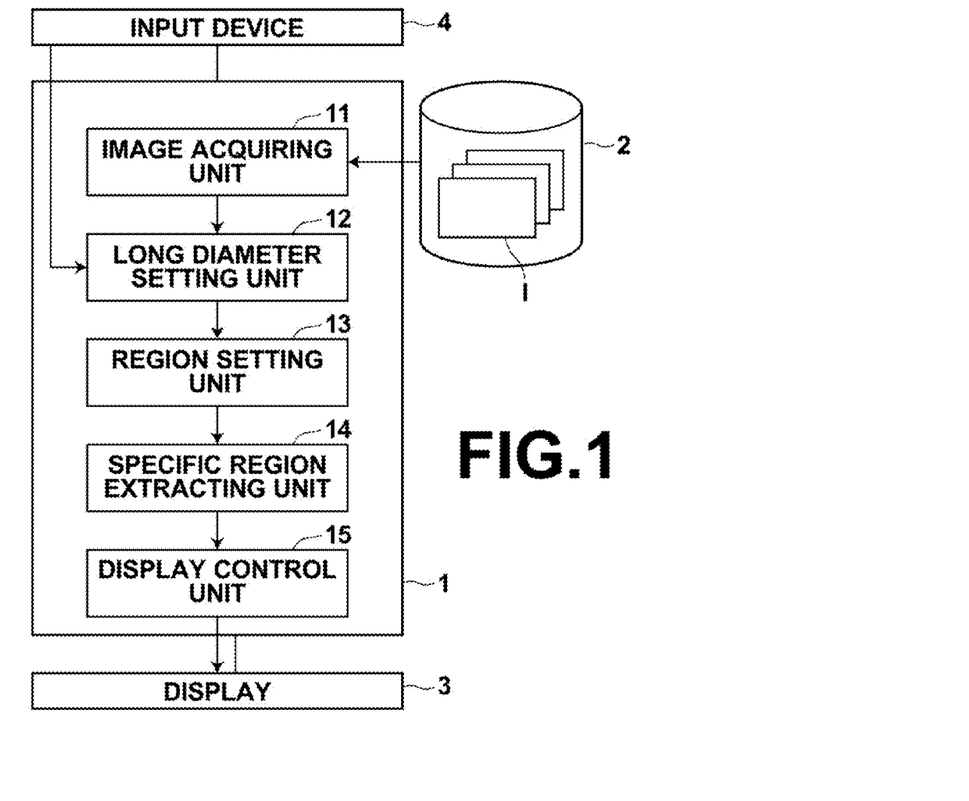
FIG. 1 is a block diagram illustrating the schematic configuration of a medical image diagnosis assisting system that uses an image processing device according to an embodiment of the present invention.

A medical image diagnosis assisting system that uses a medical image display device, method, and program according to an embodiment of the present invention is described in detail below with reference to the drawings. FIG. 1 is a block diagram illustrating the schematic configuration of the medical image diagnosis assisting system that uses this embodiment. While the present invention is applicable to various fields where processing of extracting a specific region within an input image is executed, the description given here is about an example of applying the present invention to the extraction of a tumor region in diagnostic imaging in the medical field.

The medical image diagnosis assisting system of this embodiment includes, as illustrated in FIG. 1, an image processing device 1, a medical image storing server 2, a display 3, and an input device 4.

The image processing device 1 is a computer in which an image processing program of this embodiment is installed.

The image processing device 1 includes a central processing unit (CPU), a semiconductor memory, and a medical image storing server device which is a hard disk, a solid state drive (SSD), or the like in which the image processing program of this embodiment is installed. Those hardware components form an image acquiring unit 11, a long diameter setting unit 12, a region setting unit 13, a specific region extracting unit 14, and a display control unit 15 which are illustrated in FIG. 1. The central processing unit executes the image processing program of this embodiment which is installed in the medical image storing server device, thereby putting the respective units into operation.

The image acquiring unit 11 is for acquiring, as input images I, volume data of a patient which is stored on the medical image storing server 2, and for temporarily storing the acquired data in the memory. The medical image storing server 2 stores volume data transferred from a testing department which handles photographing, or volume data acquired by a database search. The medical image storing server 2 stores medical images that are photographs of patients taken by arbitrary modalities such as CT, MRI, PET, SPECT, and ultrasound imaging, and the image acquiring unit 11 can acquire those medical images.

The image acquiring unit 11 in this embodiment acquires volume data for observing the progress of a tumor in a lung of the same patient, specifically, pieces of volume data V which are photographs of a tumor in a lung of a patient taken at different points in time. In the following description, the volume data V that is taken at a given reference time point (for example, a time point in the past) is referred to as volume data V1, and the volume data V that is taken at a time point later than the reference time point (for example, the current time) is referred to as volume data V2.

The image acquiring unit 11 in this embodiment acquires, as an input image I1, a slice image that forms the volume data V1 and acquires, as an input image I2, a slice image that forms the volume data V2. The image processing device 1 performs separate image processing procedures which are described later to the slice image I1 and the slice image I2 which form the volume data V1 and the volume data V2, respectively.

Figure 2:
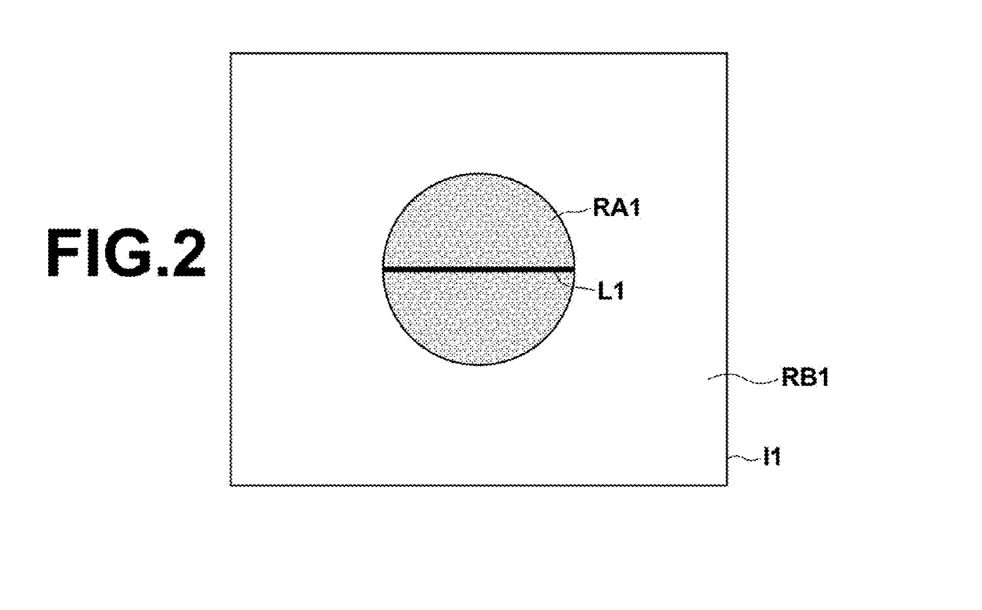
FIG. 2 is a diagram illustrating an example of a long diameter which is set in a specific region.

The long diameter setting unit 12 is for setting a long diameter L1 of a tumor region RA1 within the input image I1 acquired by the image acquiring unit 11, and a long diameter L2 of a tumor region RA2 within the input image I2 acquired by the image acquiring unit 11. In this embodiment, a user uses the input device 4 to specify two given points within the input images I1 and I2 displayed on the display 3, and the long diameter setting unit 12 acquires the coordinates of the specified points as information for identifying the long diameter L1 of the tumor region RA1 within the input image I1 and the long diameter L2 of the tumor region RA2 within the input image I2 to store the information in the memory. FIG. 2 is a diagram illustrating an example in which the long diameter L1 is set in the tumor region RA1 within the input image I1. The long diameter L2 of the tumor region RA2 within the input image I2 is set in the same manner that is illustrated in FIG. 2.

The long diameter setting unit 12 is not limited to the unit described above which just receives a manual input of settings about a long diameter, and may be a unit that automatically measures and sets the long diameters L1 and L2 by known methods.

Figure 3:
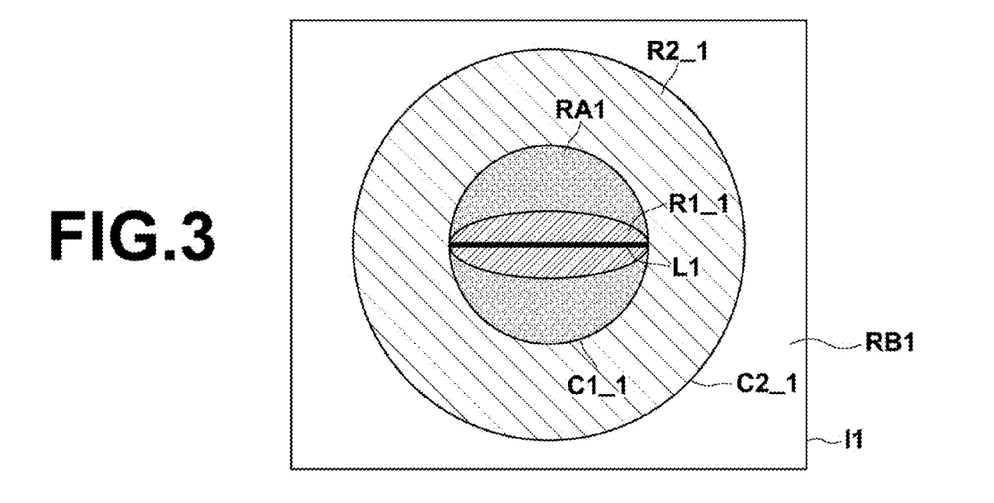
FIG. 3 is a diagram illustrating an example of a first region and a second region which are set based on the long diameter of FIG. 2.

The region setting unit 13 sets, within the input image I1, based on the long diameter L1 which is set by the long diameter setting unit 12, a first region R1_1, which is estimated as highly probable to be the tumor region RA1, and a second region R2_1, which is estimated as highly probable to be a background region RB1. The background region RB1 is a region within the input image I1 other than the tumor region RA1. FIG. 3 is a diagram illustrating an example in which the first region R1_1 and the second region R2_1 are set based on the long diameter L1 of FIG. 2.

The region setting unit 13 also sets, within the input image I2, based on the long diameter L2 which is set by the long diameter setting unit 12, a first region R1_2, which is estimated as highly probable to be the tumor region RA2, and a second region R2_2, which is estimated as highly probable to be a background region RB2. The background region RB2 is a region within the input image I2 other than the tumor region RA2.

The first region R1_1 is a region that is estimated as highly probable to be the tumor region RA1. The tumor region RA1 within the input image I1 is likely to be a region centered around the midpoint of the long diameter L1, and a region in the vicinity of the long diameter L1 is therefore estimated as likely to be the tumor region RA1. Accordingly, an elliptical region containing the vicinity of the long diameter L1 is set as the first region R1_1 in this embodiment as illustrated in FIG. 3. The minor axis of the elliptical region is set to a value that is obtained by multiplying the long diameter L1 by a given ratio. By setting as the first region R1_1 a region that is contained in the elliptical region containing the vicinity of the long diameter L1, a region that is highly probable to be the tumor region RA1 can be set as the first region R1_1 easily and favorably. An elliptical region that contains the vicinity of the long diameter L2 is set as the first region R1_2 for the same reason.

While elliptical regions that have the entire long diameter L1 and the entire long diameter L2 as their major axes are set as the first regions R1_1 and R1_2, respectively, in this embodiment, the present invention is not limited thereto. For example, partial regions of the elliptical regions may be set as the first regions R1_1 and R1_2.

The first regions R1_1 and R1_2 can be regions of any size and shape, and can be located anywhere, as long as they are regions that are estimated as highly probable to be the tumor regions RA1 and RA2 based on the long diameters L1 and L2. It is preferred for the first regions R1_1 and R1_2 to be shaped so that the vicinities of the long diameters L1 and L2 are contained and so that there is less chance of containing the background regions RB1 and RB2. Any estimation method with which the probability of being the tumor regions RA1 and RA2 can be determined is applicable. The first regions R1_1 and R1_2 may each be a single region or may each include a plurality of regions.

The second region R2_1 is a region that is estimated as highly provable to be the background region RB1. Because the tumor region RA1 is likely to be a region centered around the midpoint of the long diameter L1 as described above and it is regarded that the long diameter L1 represents the maximum diameter of the tumor region RA1, it is estimated that the tumor region RA1 is not found outside the long diameter L1, or that, outside the long diameter L1, the proportion of regions that are contained in the background region RB1 is relatively larger than the proportion of regions that are contained in the tumor region RA1.

Accordingly, by setting as the second region R2_1 a region of a given shape that is located outside a circle C1_1 whose diameter is the long diameter L1, a region highly probable to be the background region RB1 can be set easily and favorably as the second region R2_1 with the use of the information of the long diameter L1. The region of a given shape can be set as a region of any shape as long as the region is located outside the circle C1_1 and stretches to a given extent. For example, the region of a given shape can be a polygonal region, such as a rectangular region, that is located outside the circle C1_1.

In this embodiment, a ring-shaped region that stretches outside the circle C1_1 whose diameter is the long diameter L is set as the second region R2_1 as illustrated in FIG. 3. The ring-shaped region that is set as the second region R2_1 in this embodiment is between the circle C1_1 whose diameter is the long diameter L1 and a circle C2_1 whose diameter is longer than the long diameter L1. The center of the circle C2_1 is set so as to coincide with the center of the circle C1_1, and the length of the diameter of the circle C2_1 is set to a length that is obtained by multiplying the length of the set long diameter L1 by a given ratio, which is greater than 1.

In the same manner that is described above, a ring-shaped region between a circle C1_2 whose diameter is the long diameter L2 and a circle C2_2 whose diameter is longer than the long diameter L2 is set as the second region R2_2 within the input image I2.

The second regions R2_1 and R2_2 can be regions of any size and shape, and can be located anywhere, as long as they are regions that are estimated as highly probable to be non-tumor regions based on the long diameters L1 and L2. Any estimation method with which the probability of being non-tumor regions can be determined is applicable. The second regions R2_1 and R2_2 may each be a single region or may each include a plurality of regions.

The specific region extracting unit 14 is for extracting the tumor regions RA within the input images I which form pieces of the volume data V acquired by the image acquiring unit 11. The image acquiring unit 11 in this embodiment acquires the volume data V1 and the volume data V2 which are photographs of a tumor in a lung of a patient taken at different points in time as described above, and the specific region extracting unit 14 extracts the tumor region RA1 from the volume data V1 and the tumor region RA2 from the volume data V2.

A case where the specific region extracting unit 14 extracts the tumor region RA1 from the volume data V1 of a reference time point is described first.

When extracting the tumor region RA1 from the input image I1 which forms the volume data V1 of the reference time point, the specific region extracting unit 14 calculates a first histogram, which is a density histogram of the respective density values of pixels in the first region R1_1 set by the region setting unit 13, and a second histogram, which is a density histogram of the respective density values of pixels in the second region R2_1 set by the region setting unit 13, and extracts the tumor region RA1 within the input image I1 based on the first histogram and the second histogram.

More specifically, the specific region extracting unit 14 calculates, based on the first histogram and the second histogram, for each density value, a first evaluation value that indicates the likelihood that the density value represents the tumor region RA1.

Figure 4A:
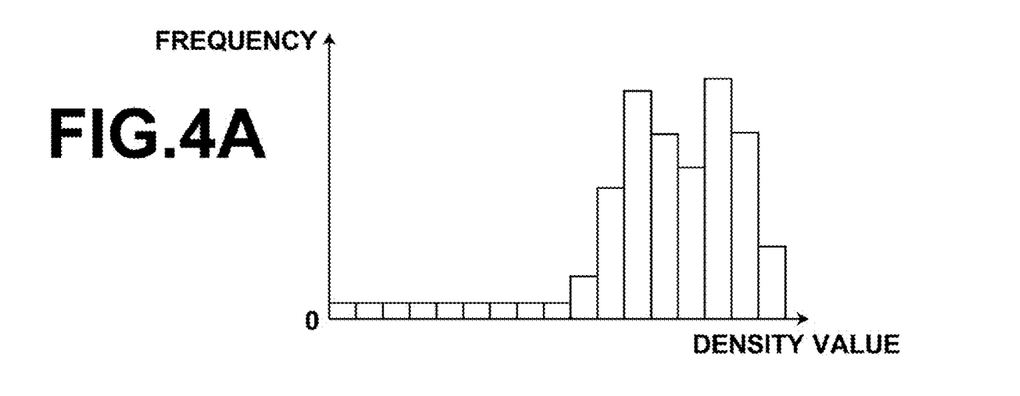
FIG. 4A is a graph showing an example of a first histogram of the first region.
Figure 4B:
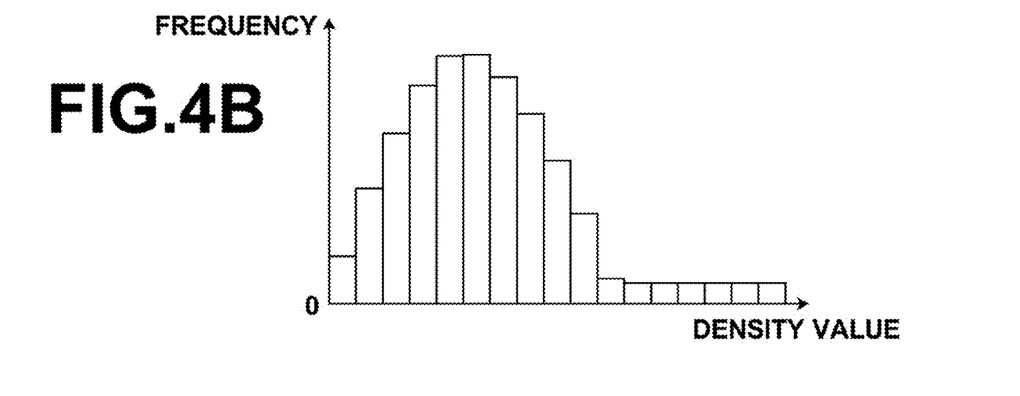
FIG. 4B is a graph showing an example of a second histogram of the second region.
Figure 4C:
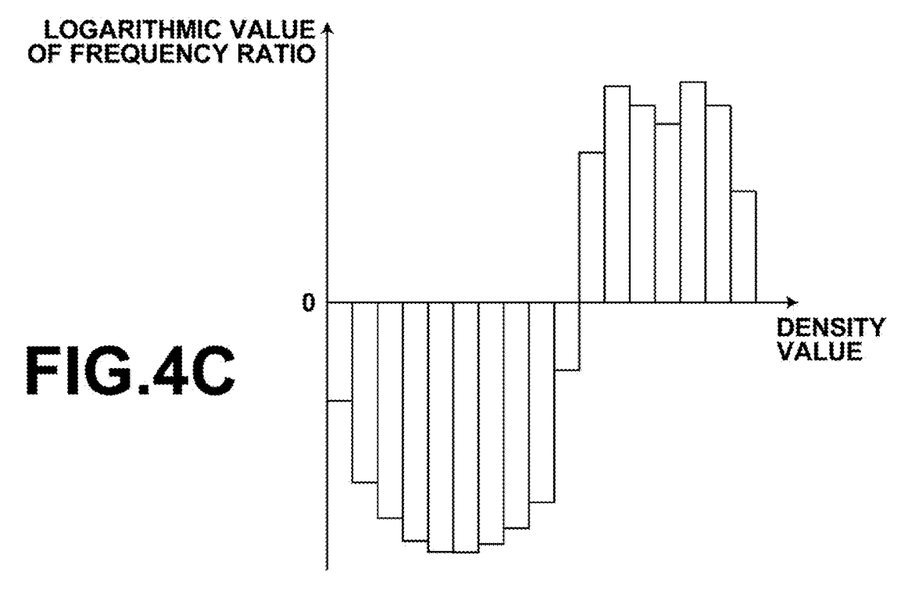
FIG. 4C is a graph showing logarithmic values of the ratio of frequencies in the first histogram of FIG. 4A to frequencies in the second histogram of FIG. 4B.

FIG. 4A is a graph showing an example of the first histogram in this embodiment. FIG. 4B is a graph showing an example of the second histogram in this embodiment. FIG. 4C is a graph showing an example of the first evaluation value in this embodiment.

The first histogram is a density histogram that is calculated by using only density values in a region highly probable to be the tumor region RA1 (the first region R1_1). The frequency of a density value in the first histogram is therefore considered as indicative of the likelihood that the density value represents the tumor region RA1. In other words, it is considered that a higher frequency in the first histogram corresponds to a density value that has a higher likelihood of representing the tumor region RA1.

The second histogram is a density histogram that is calculated by using only density values in a region highly probable to be the background region RB1 (the second region R2_1). The frequency of a density value in the second histogram is therefore considered as indicative of the likelihood that the density value represents the background region RB1. In other words, it is considered that a higher frequency in the second histogram corresponds to a density value that has a higher likelihood of representing the background region RB1. It is also considered that, when the likelihood of representing the background region RB1 increases in proportion to the frequency in the second histogram, the likelihood of representing the tumor region RA1 drops accordingly.

It is preferred for the first histogram and the second histogram to be normalized so that the scales of the histograms' vertical axes match each other and so that the scales of the histograms' horizontal axes match each other. This is because the first evaluation value which is described later is calculated by comparing the first histogram and the second histogram with each other. The first histogram and the second histogram here are normalized so that the range of density values shown in the first histogram and the range of density values shown in the second histogram match. Specifically, the density value ranges of the two histograms are adjusted appropriately so that the total number of pixels used in the calculation of the first histogram matches the total number of pixels used in the calculation of the second histogram.

In this embodiment, the first histogram and the second histogram which are calculated in the manner described above are used also when the tumor region RA2 is extracted from the volume data V2 of a time point later than the reference time point, and are therefore stored in the memory or other places.

The specific region extracting unit 14 of this embodiment calculates, for each same density value range, a logarithmic value of the ratio of a frequency value in the first histogram to a frequency value in the second histogram, and uses the calculated logarithmic value as the first evaluation value. The first evaluation value is the ratio of the likelihood of being the tumor region RA1 to the likelihood of being the background region RB1, and is accordingly considered as an indicator that indicates, for each density value, the likelihood that the density value favorably represents the tumor region RA1. For example, at a first evaluation value of 1 or more, where the likelihood of representing the tumor region RA1 is relatively higher than the likelihood of representing the background region RB1, the likelihood of representing the tumor region RA1 is evaluated as high, and it is evaluated that a larger first evaluation value indicates a higher likelihood of representing the tumor region RA1.

The first evaluation value is not limited to the mode described above, and can be any value defined by an arbitrary method based on the first histogram and the second histogram as long as the defined value indicates, for each density value, the likelihood that the density value represents a tumor region.

Alternatively, the specific region extracting unit 14 may calculate, for each same density value range, a logarithmic value of the ratio of a frequency value in the second histogram to a frequency value in the first histogram to use the calculated logarithmic value as the first evaluation value. The first evaluation value in this case is the ratio of the likelihood of being the background region RB1 to the likelihood of being the tumor region RA1. Therefore, at a first evaluation value of 1 or less, for example, the likelihood of representing the tumor region RA1 is evaluated as high, and it is considered that a larger first evaluation value indicates a lower likelihood of representing the tumor region RA1.

In this manner of calculating the first evaluation value with the use of the first histogram and the second histogram, where the first value that is an evaluation value about the likelihood of being a tumor region is calculated based on the likelihood of being the background region RB1 and the likelihood of being the tumor region RA1 both, the first evaluation value indicates with high precision the likelihood of being the tumor region RA1.

Figure 4D:
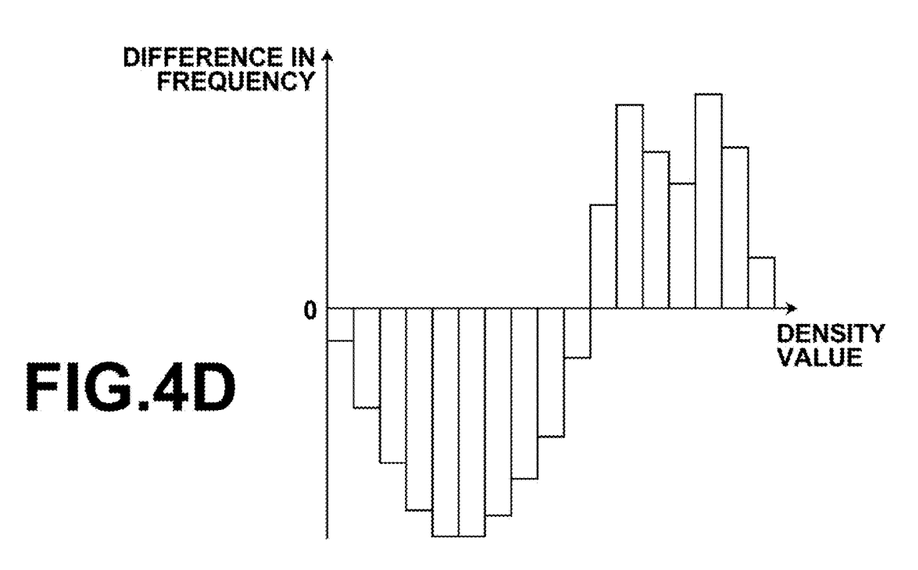
FIG. 4D is a graph showing differences between frequencies in the first histogram of FIG. 4A and frequencies in the second histogram of FIG. 4B.

The specific region extracting unit 14 may also calculate, for each same density value range, a difference between a frequency value in the first histogram and a frequency value in the second histogram to use the calculated difference as the first evaluation value. FIG. 4D shows an example of calculating a difference between a frequency value in the first histogram and a frequency value in the second histogram as the first evaluation value.

The frequency of a density value in the second histogram, which indicates the likelihood that the density value represents the background region RB1 as described above, can therefore be considered also as indicative of the likelihood that the density value does not represent the tumor region RA1. A difference between a frequency value in the first histogram and a frequency value in the second histogram accordingly indicates a difference between the likelihood of representing the tumor region RA1 and the likelihood of not representing the tumor region RA1, and the first evaluation value that is calculated as this difference indicates the likelihood of representing the tumor region RA1 as well. It is evaluated that a larger first evaluation value indicates a higher likelihood of being a specific region also when the first evaluation value is a value acquired by subtracting a frequency value in the second histogram from a frequency value in the first histogram as shown in FIG. 4D.

The specific region extracting unit 14 calculates, for every two adjacent pixels within the input image I1, a second evaluation value that indicates the likelihood that two adjacent pixels represent an outline, by acquiring the first evaluation value of each of the two adjacent pixels based on the density values of the two pixels, and calculating the second evaluation value based on the respective acquired first evaluation values of the two adjacent pixels.

The likelihood that two adjacent pixels represent an outline can be phrased as the likelihood that two adjacent pixels belong to two different regions (the tumor region RA1 and the background region RB1). It is estimated that a pixel located in the tumor region RA1 and a pixel located in the background region RB1 are likely to differ from each other in first evaluation value, which indicates the likelihood of being the tumor region RA1. Consequently, it is considered that the difference between the respective first evaluation values of two adjacent pixels is larger when one of the two adjacent pixels belongs to the tumor region RA1 and the other pixel belongs to the background region RB1, than when the two adjacent pixels both belong to the tumor region RA1 (or the background region RB1). This is utilized in this embodiment to calculate, as the second evaluation value, the absolute value of a difference between the first evaluation value of a pixel within the input image I1 and the first evaluation value of an adjacent pixel which is adjacent to the former pixel, and it is evaluated that a larger second evaluation value indicates a higher likelihood that the two adjacent pixels represent an outline.

The second evaluation value is not limited to the mode described above, and can be any value defined by an arbitrary method based on the respective first evaluation values of two adjacent pixels, as long as the defined value indicates, for every two adjacent pixels within an input image, the likelihood that the pixel pair represents an outline.

The specific region extracting unit 14 then defines a first reference vertex S that belongs to the tumor region RA1, a second reference vertex T that belongs to the background region RB1, and a plurality of vertices Nij respectively representing pixels within the input image I1. The specific region extracting unit 14 sets a connection cost, which indicates how likely the respective vertices are to be connected to each other, based on the second evaluation value, and connects the plurality of vertices to each other based on the connection cost, to thereby extract the tumor region RA1.

Figure 5:
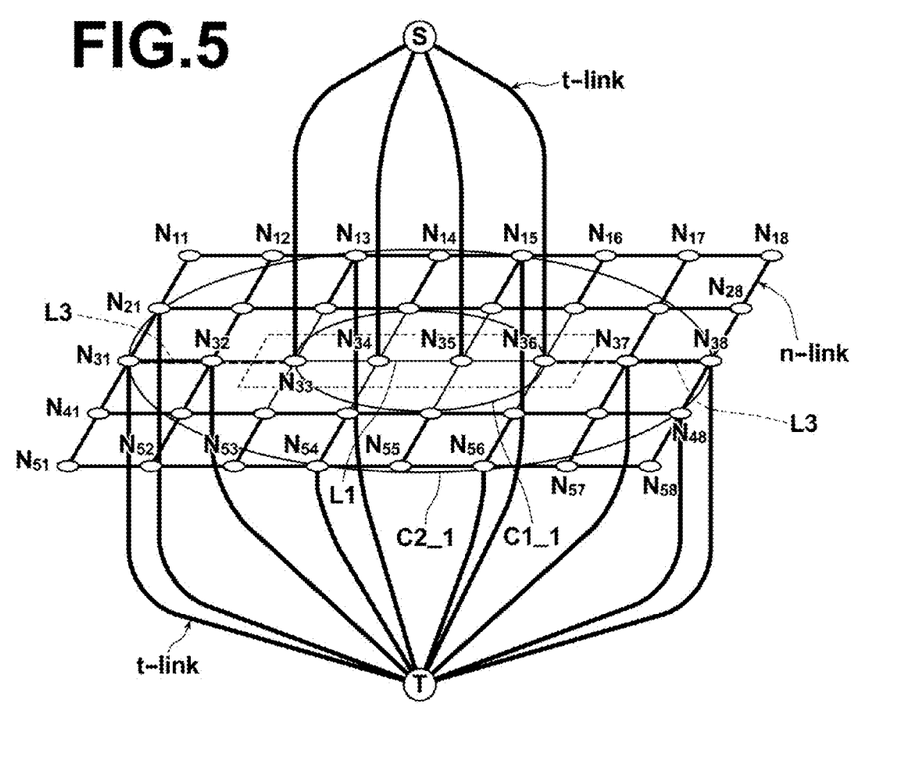
FIG. 5 is a diagram illustrating processing of extracting a specific region by graph cut.

The specific region extracting unit 14 in this embodiment defines the input image I1 as a graph that includes, as illustrated in FIG. 5, the first reference vertex S (vertex S) belonging to the tumor region RA1, the second reference vertex T (vertex T) belonging to the background region RB1, the plurality of vertices $N_{ij}$ respectively representing pixels within the input image I1, and sides each connecting the plurality of vertices to each other, sets the connection cost based on the second evaluation value so that a higher likelihood that two adjacent pixels represent an outline equals a lower likelihood of connecting a vertex that corresponds to one of the two pixels to a vertex that corresponds to the adjacent pixel, and extracts the tumor region RA1 from the graph by graph cut, based on the connection cost.

The intervals between vertices and the count of vertices in the graph of FIG. 5 are simplified for the sake of description. Details of graph cut can be found in Patent Literature 1 as well.

More specifically, when the entire region of the input image I1 is set as a determination region D, the specific region extracting unit 14 first creates a graph that includes, as illustrated in FIG. 5, the vertices $N_{ij}$ representing pixels in the determination region D, the vertices S and T which indicate labels that the pixels can have, n-links which are sides connecting vertices of adjacent pixels to each other, and t-links which are sides that connect the vertices $N_{ij}$ representing pixels to the vertex S representing the specific region, or to the vertex T representing the background region RB1.

The n-links indicate the likelihood that adjacent pixels are pixels of the same region by the size of the connection cost (the thickness of the sides in FIG. 5). The connection cost of each n-link here is set, based on the second evaluation value, so that a higher likelihood that two adjacent pixels represent an outline equals a lower likelihood of connecting vertices that correspond to the two adjacent pixels to each other (equals a thinner side). This connection cost of the n-link may further be weighted based on the distance between the adjacent pixels, a difference in density value between the adjacent pixels, or the like. The thickness of the side between vertices here indicates the size of the connection cost, and a higher connection cost is set to a thicker side.

The t-links that connect the vertices $N_{ij}$ representing pixels to the vertex S representing the tumor region RA1 indicate, for each pixel, the likelihood that the pixel is contained in the tumor region RA1. The t-links that connect the vertices $N_{ij}$ representing pixels to the vertex T representing the background region RB1 indicate, for each pixel, the likelihood that the pixel is contained in the background region RB1.

In this embodiment, when a pixel in question can be determined as one belonging to the tumor region RA1 by utilizing the information that identifies the long diameter L1 set by the long diameter setting unit 12, the connection cost of the relevant t-link is set so that a vertex corresponding to the pixel is more likely to be connected to the vertex S representing the tumor region RA1 (so that a thick side connects a vertex corresponding to the pixel to the vertex S representing the tumor region RA1). When a pixel in question can be determined as one belonging to the background region RB1, the connection cost of the relevant t-link is set so that a vertex corresponding to the pixel is more likely to be connected to the vertex T representing the background region RB1 (so that a thick side connects a vertex corresponding to the pixel to the vertex T representing the background region RB1).

Specifically, the connection cost of each t-link is set based on the following four conditions (1) to (4).

(1) For vertices corresponding to pixels that are located along the long diameter L1 and vertices corresponding to pixels that are located in the first region R1_1 (first vertices), the connection cost is set so that the vertices are more likely to be connected to the vertex S, because those pixels are likely to belong to the tumor region RA1.

(2) For vertices corresponding to pixels that are located along an extended line of the long diameter L1 and outside the ends of the long diameter L1 (second vertices which are vertices located along a broken line L3 in FIG. 5), the connection cost is set so that the vertices are more likely to be connected to the vertex T, because those pixels are likely to belong to the background region RB1.

(3) For vertices corresponding to pixels that are located on an outer outline of the second region R2_1 within the input image (third vertices which are vertices located on the circumference of the circle C2_1 in FIG. 5), the connection cost is set so that the vertices are more likely to be connected to the vertex T, because those pixels are likely to belong to the background region RB1 (a region other than the specific region).

(4) For vertices that are none of the first to third vertices out of the vertices forming the graph that represents the input image, the connection cost is set so that the vertices are less likely to be connected to the vertex S and to the vertex T both.

In the example of FIG. 5, vertices N33, N34, N35, and N36 qualify as the first vertices, and are connected to the vertex S based on Condition (1). Vertices N31, N32, N37, and N38 qualify as the second vertices, and are connected to the vertex T based on Condition (2). Vertices N13, N15, N21, N48, N54, and N56 qualify as the third vertices, and are connected to the vertex T based on Condition (3). Vertices in FIG. 5 that qualify as none of the first to third vertices are set so as not to be connected to any of the vertex S and the vertex T (so that the connection cost is 0).

It is estimated that the tumor region RA1 is likely to stretch outward from the long diameter L1 as its center. Accordingly, when vertices located along the long diameter L1 (the first vertices) are determined as likely to belong to the tumor region RA1 and the connection cost is set so that the first vertices are more likely to be connected to the vertex S as in Condition (1), the tumor region RA1 can be extracted with high precision from a graph that represents an input image by favorably utilizing the information that identifies the set long diameter L1.

Instead of Condition (I), the connection cost may be determined by an arbitrary method based on the set long diameter L1 so that vertices within a given range from the long diameter L1 are more likely to be connected to the vertex S. The given range can be set to an arbitrary range where the likelihood of belonging to the tumor region is high, and a range that is a short distance from the long diameter L1 is preferred as the given range.

The long diameter L1 is deemed as the maximum diameter of the tumor region RA1 in a direction in which the long diameter L1 extends, and it is therefore considered that the tumor region RA1 is less likely to be outside the ends of the long diameter L1 in the direction in which the long diameter L1 extends. Accordingly, the tumor region RA1 can be extracted with high precision from a graph that represents an input image by favorably utilizing the information that identifies the set long diameter L1 also when vertices located along an extended line of the long diameter L1 and outside the ends of the long diameter L1 (the second vertices) are determined as likely to belong to the background region RB1 and the connection cost is set so that the second vertices are more likely to be connected to the vertex T as in Condition (2).

Instead of Condition (2), the connection cost may be set by an arbitrary method based on the set long diameter L1 so that vertices corresponding to pixels that are located outside the ends of the long diameter L1 in the direction in which the long diameter L1 extends are more likely to be connected to the vertex T.

Vertices located in a region that is sufficiently far from the set long diameter L1 are likely to belong to background region RB1. Accordingly, when vertices located along the outer outline of the second region R2_1, which is a region highly probable to be the background region RB1, (the third vertices) are determined as likely to belong to the background region RB1 and the connection cost is set so that the third vertices are more likely to be connected to the vertex T as in Condition (3), the tumor region RA1 can be extracted with high precision from a graph that represents an input image by favorably utilizing the information that identifies the set long diameter L1, because the third vertices are located sufficiently far from the long diameter L1.

Instead of Condition (3), the connection cost may be determined by an arbitrary method based on the set long diameter L1 so that vertices that are at a given distance or more from the long diameter L1 are more likely to be connected to the vertex T. The given distance can be set to an arbitrary range where the likelihood of belonging to the background region RB1 is high, and a range that is a great distance from the long diameter L1 is preferred as the given distance.

The connection costs of the t-links are not limited to the mode described in this embodiment, and can be set by any method as long as the connection costs of the t-links are set so that the tumor region RA1 and the background region RB1 can be separated from each other. Some or all of the connection cost settings based on Conditions (1) to (4) may therefore be omitted, or replaced by other methods, as long as the set connection costs of the t-links ensure that the tumor region RA1 and the background region RB1 can be separated from each other.

In the case where information about which of the tumor region RA1 and the background region RB1 a pixel in question represents is already given, the connection cost settings of the t-links described above can be set by any method based on the given information. In the case where the information is not given, the connection cost may be calculated based on statistical characteristics of density values in one or more pixels for which whether the pixel represents the tumor region RA1 or the background region RB1 is known.

The specific region extracting unit 14 executes region segmentation by minimizing an evaluation function F, which indicates the sum of the connection costs of the t-links and the n-links in the graph described above, with the use of a known method that is applicable to graph cut such as maximum flow-minimum cut. Consequently, appropriate links out of all t-links and n-links are cut as indicated by the dotted line in FIG. 5 to separate the vertex S from the vertex T, and the input image is divided into the tumor region RA1 and the background region RB1.

The steps executed by the specific region extracting unit 14 to extract the tumor region RA1 from the volume data V1 of the reference time point have now been described.

Described next is a case where the specific region extracting unit 14 extracts the tumor region RA2 from the volume data V2 of a time point later than the reference time point.

When extracting the tumor region RA2 from the volume data V2 of a time point later than the reference time point, the specific region extracting unit 14 uses the first histogram and the second histogram that are used in the extraction described above of the tumor region RA1 from the volume data V1 of the reference time point. The first histogram and the second histogram are density histograms of the first region R1_1 and the second region R2_1, respectively, within the input image I1.

In other words, the specific region extracting unit 14 uses the same first histogram and second histogram in the extraction of the tumor region RA1 from the input image I1 which forms the volume data V1 of the reference time point and in the extraction of the tumor region RA2 from the input image I2 which forms the volume data V2 of a time point later than the reference time point, both.

More specifically, the specific region extracting unit 14 extracts the tumor region RA2 within the input image I2 by reading the first histogram and the second histogram which have been stored when the tumor region RA1 has been extracted from the input image I1, and calculating, for each density value, a first evaluation value that indicates the likelihood that the density value represents the tumor region RA2, based on the first histogram and the second histogram. The first evaluation value is calculated in the same way as in the extraction of the tumor region RA1 from the input image I1.

The specific region extracting unit 14 calculates, for every two adjacent pixels within the input image I2, a second evaluation value that indicates the likelihood that two adjacent pixels represent an outline, by acquiring the first evaluation value of each of the two adjacent pixels based on the density values of the two pixels, and calculating the second evaluation value based on the respective acquired first evaluation values of the two adjacent pixels. The second evaluation value is also calculated in the same way as in the extraction of the tumor region RA1 from the input image I1.

As in the extraction of the tumor region RA1 from the input image I1, the specific region extracting unit 14 then defines a first reference vertex S that belongs to the tumor region RA2, a second reference vertex T that belongs to the background region RB2, and a plurality of vertices Nij representing pixels within the input image I2. The specific region extracting unit 14 sets a connection cost, which indicates how likely the respective vertices are to be connected to each other, based on the second evaluation value, and connects the plurality of vertices to each other based on the connection cost, to thereby extract the tumor region RA2.

The connection cost is set by the same method that is used in the extraction described above of the tumor region RA1 from the input image I1. However, the connection cost of the t-links that connect the vertices $N_{ij}$ representing pixels to the vertex S representing the tumor region RA2 and the connection cost of the t-links that connect the vertices $N_{ij}$ representing pixels to the vertex T representing the background region RB2 are set with the use of the long diameter L2 of the tumor region RA2 which is set within the input image I2, instead of the long diameter L1 of the tumor region RA1 which is set within the input image I1, and with the use of the first region R1_2 and the second region R2_2 which are set within the input image I2, instead of the first region R1_1 and the second region R2_1 which are set within the input image I1.

The specific region extracting unit 14 then extracts the tumor region RA2 from the input image I2 by graph cut as in the extraction of the tumor region RA1 from the input image I1.

The steps executed by the specific region extracting unit 14 to extract the tumor region RA2 from the volume data V2 of a time point later than the reference time point have now been described.

The display control unit 15 is for displaying on the display 3 the input images I1 and I2, various images created in the process of the image processing described above, the extracted tumor regions RA1 and RA2, and others suitably as the need arises, for example, in response to a user's instruction or a request made by a program.

Figure 6:
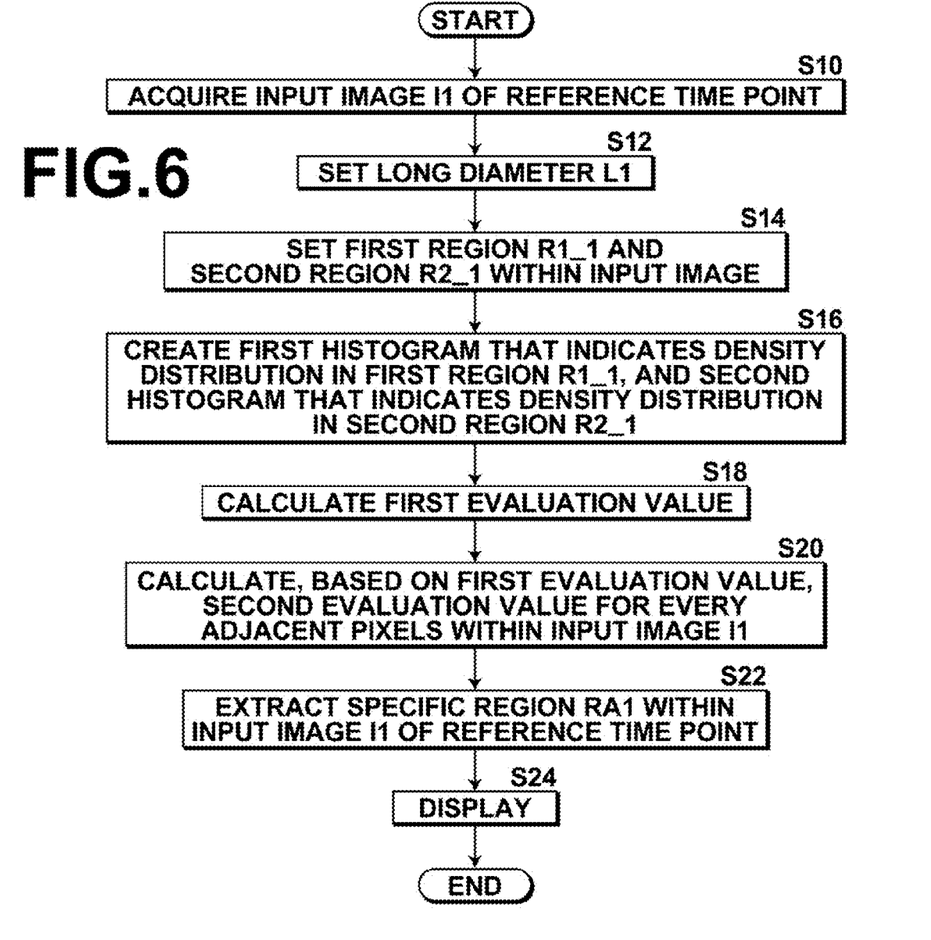
FIG. 6 is a flow chart illustrating the flow of processing of extracting a tumor region RA1 from an input image I1 of a reference time point.

FIG. 6 is a flow chart illustrating the flow of processing that is executed by the image processing device 1 of this embodiment to extract the tumor region RA1 from the input image I1, which forms the volume data V1 of the reference time point. Processing steps of the image processing device 1 of this embodiment are sequentially described below with reference to FIG. 6.

First, the image acquiring unit 11 acquires from the medical image storing server 2 the input image I1, which forms the volume data V1 taken at the reference time point (S10). Next, the long diameter setting unit 12 sets the long diameter L1 based on an instruction input by the user about the long diameter (S12). Based on the set long diameter L1, the region setting unit 13 sets the first region R1_1, which is an elliptical region having the long diameter L1 as its major axis, and the second region R2_1, which is a ring-shaped region between the circle C1_1 having the long diameter L1 as its diameter and the circle C2_1 (S14).

Next, the specific region extracting unit 14 creates the first histogram based on the respective density values of pixels in the first region R1_1, creates the second histogram based on the respective density values of pixels in the second region R2_1, and normalizes the first histogram and the second histogram (S16). The specific region extracting unit 14 calculates, for each density value, a logarithmic value of the ratio of a frequency value in the first histogram to a frequency value in the second histogram, as the first evaluation value which indicates the likelihood that the density value represents the tumor region RA1 (S18). The specific region extracting unit 14 further calculates, for every two adjacent pixels within the input image I1, the absolute value of a difference between the respective first evaluation values of the two adjacent pixels, as the second evaluation value which indicates the likelihood of representing an outline (S20).

The specific region extracting unit 14 next defines the input image I1 as a graph that includes the first reference vertex S belonging to the tumor region RA1, the second reference vertex T belonging to the background region RB1, a plurality of vertices representing pixels within the input image I1, and sides each connecting the plurality of vertices to each other. Based on the second evaluation value, the connection cost of each n-link is set so that vertices that correspond to two adjacent pixels are less likely to be connected to each other as the likelihood that the two adjacent pixels represent an outline becomes higher. The connection cost of each t-link is also set, based on the set long diameter L1, so that the first vertices that are estimated as belonging to the tumor region RA1 are connected to the vertex S that represents the tumor region RA1, and so that the second vertices and third vertices that are estimated as belonging to the background region RB1 are connected to the vertex T that represents the background region RB1. The specific region extracting unit 14 then divides the graph by minimizing the evaluation function F based on the connection costs, and thus extracts the tumor region RA1 from the input image I1 (S22).

Figure 7:
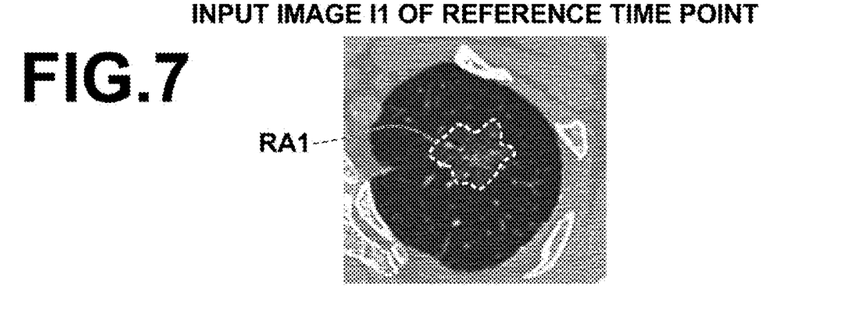
FIG. 7 is an image showing an example of the tumor region RA1 which is extracted from the input image I1 of the reference time point.

The display control unit 15 displays the extracted tumor region RA1 on the display (S24), and the processing is ended. An example of the tumor region RA1 that is extracted by region segmentation in the manner described above is shown in FIG. 7.

Figure 8:
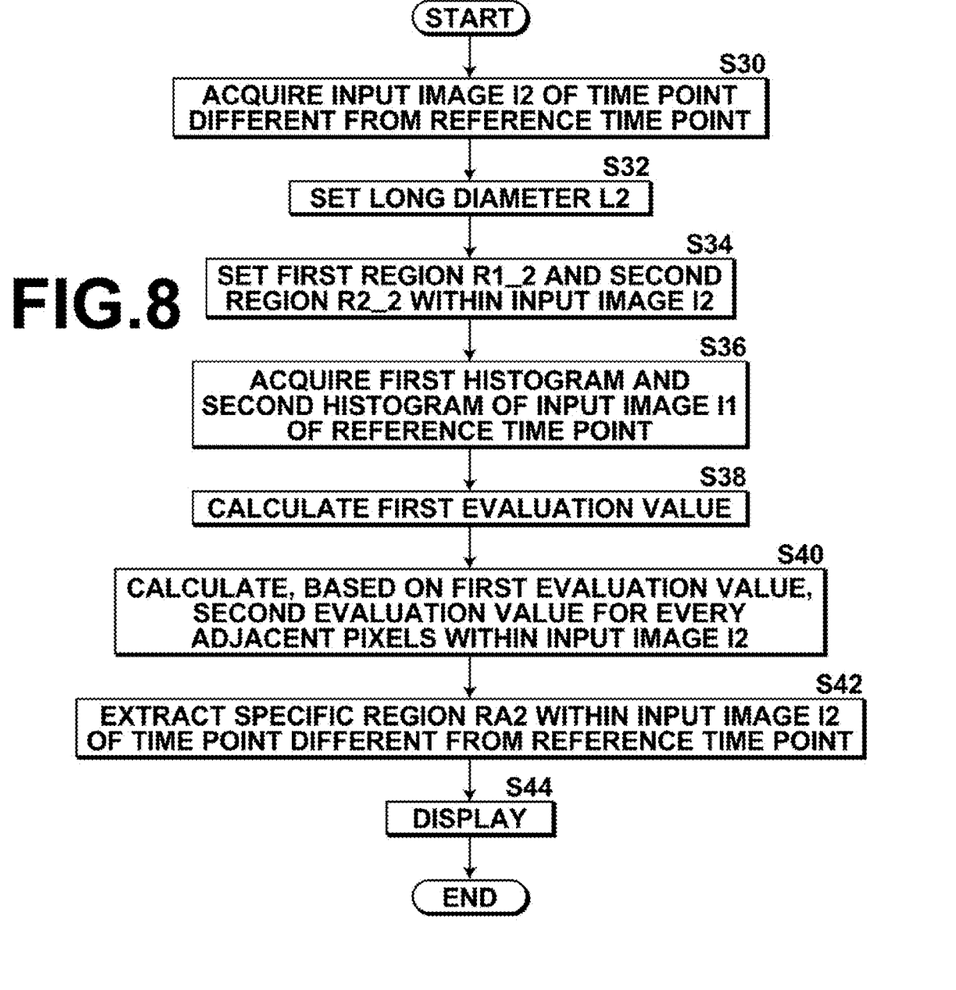
FIG. 8 is a flow chart illustrating the flow of processing of extracting a tumor region RA2 from an input image I2 of a time point different from the reference time point.

FIG. 8 is a flow chart illustrating the flow of processing that is executed by the image processing device 1 of this embodiment to extract the tumor region RA2 from the input image I2, which forms the volume data V2 taken at a time point later than the reference time point. Processing steps of the image processing device 1 of this embodiment are sequentially described below with reference to FIG. 8.

First, the image acquiring unit 11 acquires from the medical image storing server 2 the input image I2, which forms the volume data V2 taken at the time point later than the reference time point (S30). Next, the long diameter setting unit 12 sets the long diameter L2 based on an instruction input by the user about the long diameter (S32). Based on the set long diameter L2, the region setting unit 13 sets the first region R1_2, which is an elliptical region having the long diameter L2 as its major axis, and the second region R2_2, which is a ring-shaped region between the circle C1_2 having the long diameter L2 as its diameter and the circle C2_2 (S34).

Next, the specific region extracting unit 14 acquires the first histogram and the second histogram which have been created when extracting the tumor region RA1 from the input image I1 (S36). The specific region extracting unit 14 calculates, for each density value, a logarithmic value of the ratio of a frequency value in the first histogram to a frequency value in the second histogram, as the first evaluation value which indicates the likelihood that the density value represents the tumor region RA2 (S38). The specific region extracting unit 14 further calculates, for every two adjacent pixels within the input image I2, the absolute value of a difference between the respective first evaluation values of the two adjacent pixels, as the second evaluation value which indicates the likelihood of representing an outline (S40).

The specific region extracting unit 14 next defines the input image I2 as a graph that includes the first reference vertex S belonging to the tumor region RA2, the second reference vertex T belonging to the background region RB2, a plurality of vertices representing pixels within the input image I2, and sides each connecting the plurality of vertices to each other. Based on the second evaluation value, the connection cost of each n-link is set so that vertices that correspond to two adjacent pixels are less likely to be connected to each other as the likelihood that the two adjacent pixels represent an outline becomes higher. The connection cost of each t-link is also set, based on the set long diameter L2, so that the first vertices that are estimated as belonging to the tumor region RA2 are connected to the vertex S that represents the tumor region RA2, and so that the second vertices and third vertices that are estimated as belonging to the background region RB2 are connected to the vertex T that represents the background region RB2. The specific region extracting unit 14 then divides the graph by minimizing the evaluation function F based on the connection costs, and thus extracts the tumor region RA2 from the input image I2 (S42).

Figure 9:
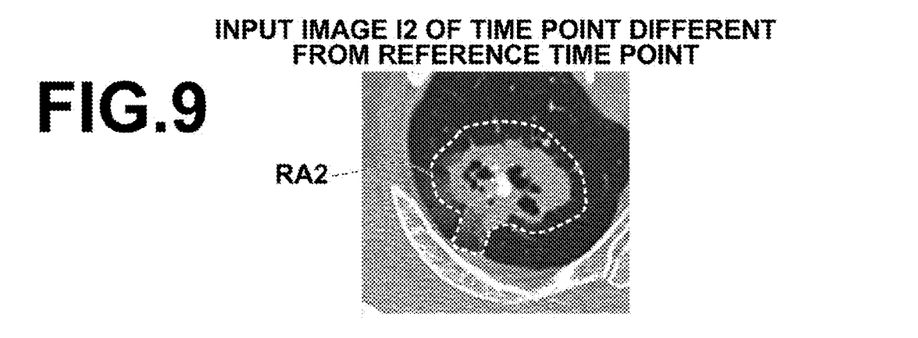
FIG. 9 is an image showing an example of the tumor region RA2 which is extracted from the input image I2 of a time point different from the reference time point.

The display control unit 15 displays the extracted tumor region RA2 on the display (S44), and the processing is ended. An example of the tumor region RA2 that is extracted by region segmentation in the manner described above is shown in FIG. 9.

According to the medical image diagnosis assisting system of this embodiment, a first region estimated as highly probable to be a tumor region and a second region estimated as highly probable to be a background region, which is a region other than the tumor region, are set within an input image photographed at a reference time point, a first histogram which is a density histogram in the first region and a second histogram which is a density histogram in the second region are calculated, the tumor region within the input image that is photographed at the reference time point is extracted based on the first histogram and the second histogram, and a tumor region corresponding to the tumor region within the input image that is photographed at the reference time point is extracted, based on the first histogram and the second histogram, from an input image that is photographed at a time point different from the reference time point. Tumor regions can thus be extracted with the use of the same standard in the case when specific regions are extracted from the input image that is photographed at the reference time point and in the case where specific regions are extracted from the input image that is photographed at a time point different from the reference time point, by using the first histogram and the second histogram in both cases.

Consequently, portions where the symptom has progressed to approximately the same degree can be extracted as tumor regions respectively from the input image photographed at the reference time point and the input image photographed at a time point different from the reference time point, and an exact change in size between those regions can be grasped.

Figure 10:
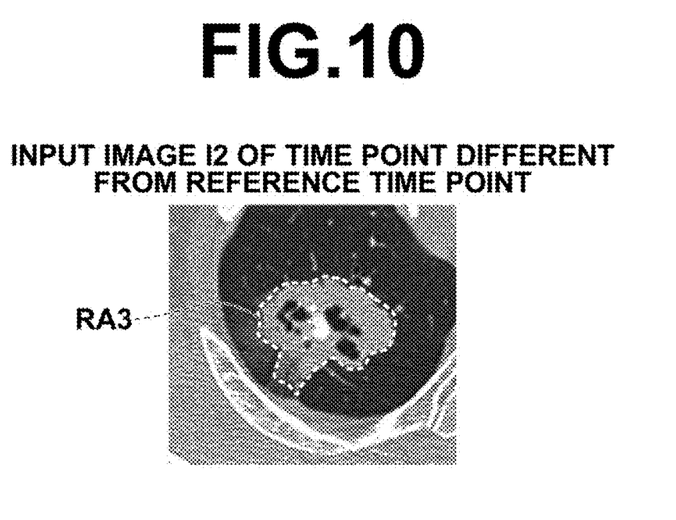
FIG. 10 is an image showing an example of extracting a tumor region RA3 with the use of a first histogram and a second histogram that are calculated from the input image I2 of a time point different from the reference time point.

FIG. 10 shows an example in which a tumor region RA3 is extracted by using, when extracting a tumor region from the input image I2 which is photographed at a time point different from the reference time point, a first histogram and a second histogram that are calculated from the input image I2 of the time point different from the reference time point, instead of using the first histogram and the second histogram that are calculated from the input image I1 of the reference time point. As can be seen in FIG. 10, when the tumor region RA3 is extracted with the use of the first histogram and the second histogram that are calculated from the input image I2, only a portion where the symptom has progressed and the density has dropped (a portion turned to white) is extracted as the tumor region RA3, thereby making the extracted region smaller than the tumor region RA2 of FIG. 9, which is the correctly extracted region.

While a tumor region is extracted as a specific region in the embodiment described above, the present invention is not limited thereto and a blood vessel region may be extracted instead. In the case of a blood vessel region, plaques increase with the progress of the symptom, and portions of the plaques are low in density on an image.

Accordingly, in the case of extracting blood vessel regions respectively from input images that are photographed at different points in time, for example, corresponding blood vessel regions cannot be extracted appropriately if the first histogram and the second histogram that are calculated from one of the input images are used in the extraction of one blood vessel region whereas the first histogram and the second histogram that are calculated based on another of the input images are used in the extraction of another blood vessel region, because the fluctuation in plaque size makes the extraction standard vary.

The corresponding blood vessel regions can be extracted appropriately by using, as in the medical image diagnosis assisting system of the embodiment described above, the first histogram and the second histogram that are calculated from the input image photographed at the reference time point to extract a blood vessel region from the input image of a time point different from the reference time point. When extracting the blood vessel regions, the region setting unit 13 sets a long diameter in a sectional image that is orthogonal to a direction in which the blood vessel extends.

While a specific region is extracted by graph cut in the embodiment described above, other methods than graph cut may be used. For example, a specific region may be extracted by performing, for each pixel within an input image, threshold processing on the first evaluation value that is associated with the pixel. In the case of extracting a specific region by threshold processing as this, there is a chance that irrelevant portions such as a bone contained in the background region which is a region other than the specific region, are extracted as a part of the specific region, and it is therefore desirable to calculate the first evaluation value by weighting based on the distance between the first region and the second region, which are set by the region setting unit 13, or the like. Alternatively, threshold processing may be performed after the calculated first evaluation value is weighted based on the distance between the first region and the second region or the like.

Each embodiment described above is merely an example, and all of the description given above are not to be used to interpret the technical scope of the present invention in a limited manner.

The technical scope of the present invention encompasses various modifications that are made, without departing from the spirit of the present invention, to the system configuration, hardware configuration, processing flows, module configurations, user interface, processing specifics, and the like of the embodiment described above.

The image processing device 1 may distribute the functions of the units described above among a plurality of computers. Any known devices can be employed as the input device, display, and other constituent devices of the system.

What is claimed is:

1. An image processing device, comprising:
an image acquiring unit for acquiring a plurality of input images of the same subject photographed at different points in time;
a region setting unit for setting, within an input image that is photographed at a reference time point out of the plurality of input images acquired by the image acquiring unit, a first region estimated as highly probable to be a specific region and a second region estimated as highly probable to be a background region, which is a region other than the specific region; and
a specific region extracting unit for calculating a first histogram, which is a density histogram of respective density values of pixels in the first region, and a second histogram, which is a density histogram of respective density values of pixels in the second region, and extracting the specific region within the input image that is photographed at the reference time point, based on the first histogram and the second histogram,
wherein, based on the first histogram and the second histogram which are calculated with use of the input image photographed at the reference time point, the specific region extracting unit extracts a specific region corresponding to the specific region within the input image that is photographed at the reference time point from one of the plurality of input images that is photographed at a time point different from the reference time point, and
wherein the specific region extracting unit is configured to:
calculate, for each density value, based on the first histogram and the second histogram, a first evaluation value which indicates a likelihood that the density value represents the specific region;
calculate, for every two adjacent pixels within the input image, a second evaluation value which indicates a likelihood that the two adjacent pixels represent an outline, based on the respective first evaluation values of the density values of the two adjacent pixels; and
define a first reference vertex which belongs to the specific region, a second reference vertex which belongs to the background region, and a plurality of vertices respectively representing the pixels within the input image, set a connection cost, which indicates how likely the plurality of vertices are to be connected to each other, based on the second evaluation value, and connect the vertices to each other based on the set connection cost, thereby extracting the specific region.

2. An image processing device according to claim 1, wherein the specific region extracting unit calculates the first evaluation value based on a ratio of a frequency value in the first histogram and a frequency value in the second histogram.

3. An image processing device according to claim 1, wherein the specific region extracting unit calculates the first evaluation value based on a difference between a frequency value in the first histogram and a frequency value in the second histogram.

4. An image processing device according to claim 1, wherein the specific region extracting unit calculates, for each pixel within the input image, the second evaluation value so that the likelihood that the two adjacent pixels represent an outline becomes higher as a difference between the first evaluation values of the two adjacent pixels becomes larger.

5. An image processing device according to claim 2, wherein the specific region extracting unit calculates, for each pixel within the input image, the second evaluation value so that the likelihood that the two adjacent pixels represent an outline becomes higher as a difference between the first evaluation values of the two adjacent pixels becomes larger.

6. An image processing device according to claim 3, wherein the specific region extracting unit calculates, for each pixel within the input image, the second evaluation value so that the likelihood that the two adjacent pixels represent an outline becomes higher as a difference between the first evaluation values of the two adjacent pixels becomes larger.

7. An image processing device according to claim 1, wherein, based on the second evaluation value, the specific region extracting unit sets the connection cost so that the vertices corresponding to the two adjacent pixels become less likely to be connected to each other as the likelihood that the two adjacent pixels represent an outline becomes higher.

8. An image processing device according to claim 2, wherein, based on the second evaluation value, the specific region extracting unit sets the connection cost so that the vertices corresponding to the two adjacent pixels become less likely to be connected to each other as the likelihood that the two adjacent pixels represent an outline becomes higher.

9. An image processing device according to claim 3, wherein, based on the second evaluation value, the specific region extracting unit sets the connection cost so that the vertices corresponding to the two adjacent pixels become less likely to be connected to each other as the likelihood that the two adjacent pixels represent an outline becomes higher.

10. An image processing device according to claim 4, wherein, based on the second evaluation value, the specific region extracting unit sets the connection cost so that the vertices corresponding to the two adjacent pixels become less likely to be connected to each other as the likelihood that the two adjacent pixels represent an outline becomes higher.

11. An image processing device according to claim 1, further comprising a long diameter setting unit for setting a long diameter of the specific region within the input image that is photographed at the reference time point,
  wherein the region setting unit sets the first region and the second region based on the long diameter received by the long diameter setting unit.

12. An image processing device according to claim 1, further comprising a long diameter setting unit for setting a long diameter of the specific region within the input image that is photographed at the reference time point,
  wherein the specific region extracting unit sets the connection cost so that the vertices that are within a given range from the long diameter are more likely to be connected to the first reference vertex.

13. An image processing device according to claim 1, further comprising a long diameter setting unit for setting a long diameter of the specific region within the input image that is photographed at the reference time point,
  wherein the specific region extracting unit sets the connection cost so that the vertices that correspond to pixels located outside two ends of the long diameter in a direction in which the long diameter extends are more likely to be connected to the second reference vertex.

14. An image processing device according to claim 11, wherein the region setting unit sets, as the first region, a region contained in an elliptical region that has the long diameter as its major axis.

15. An image processing device according to claim 11, wherein the region setting unit sets, as the second region, a region of a given shape that is located outside a circle whose diameter is the long diameter.

16. An image processing device according to claim 1, wherein the specific region comprises a tumor region or a blood vessel region.

17. An image processing method, comprising:
  acquiring a plurality of input images of the same subject photographed at different points in time;
  setting, within an input image that is photographed at a reference time point out of the plurality of acquired input images, a first region estimated as highly probable to be a specific region and a second region estimated as highly probable to be a background region, which is a region other than the specific region;
  calculating a first histogram, which is a density histogram of respective density values of pixels in the first region, and a second histogram, which is a density histogram of respective density values of pixels in the second region, and extracting the specific region within the input image that is photographed at the reference time point, based on the first histogram and the second histogram; and
  extracting, based on the first histogram and the second histogram which are calculated with use of the input image photographed at the reference time point, a specific region corresponding to the specific region within the input image that is photographed at the reference time point from one of the plurality of input images that is photographed at a time point different from the reference time point,
  wherein the extracting includes:
    calculating, for each density value, based on the first histogram and the second histogram, a first evaluation value which indicates a likelihood that the density value represents the specific region;
    calculating, for every two adjacent pixels within the input image, a second evaluation value which indicates a likelihood that the two adjacent pixels represent an outline, based on the respective first evaluation values of the density values of the two adjacent pixels; and
    defining a first reference vertex which belongs to the specific region, a second reference vertex which belongs to the background region, and a plurality of vertices respectively representing the pixels within the input image, set a connection cost, which indicates how likely the plurality of vertices are to be connected to each other, based on the second evaluation value, and connect the vertices to each other based on the set connection cost, thereby extracting the specific region.

18. A non-transitory computer-readable recording medium containing a program for causing a computer to execute the procedures of:
  acquiring a plurality of input images of the same subject photographed at different points in time;
  setting, within an input image that is photographed at a reference time point out of the plurality of acquired input images, a first region estimated as highly probable to be a specific region and a second region estimated as highly probable to be a background region, which is a region other than the specific region;
  calculating a first histogram, which is a density histogram of respective density values of pixels in the first region, and a second histogram, which is a density histogram of respective density values of pixels in the second region, and extracting the specific region within the input image that is photographed at the reference time point, based on the first histogram and the second histogram; and
  extracting, based on the first histogram and the second histogram which are calculated with use of the input image photographed at the reference time point, a specific region corresponding to the specific region within the input image that is photographed at the reference time point from one of the plurality of input images that is photographed at a time point different from the reference time point,
  wherein the extracting includes:
    calculating, for each density value, based on the first histogram and the second histogram, a first evaluation value which indicates a likelihood that the density value represents the specific region;
    calculating, for every two adjacent pixels within the input image, a second evaluation value which indicates a likelihood that the two adjacent pixels represent an outline, based on the respective first evaluation values of the density values of the two adjacent pixels; and
    defining a first reference vertex which belongs to the specific region, a second reference vertex which belongs to the background region, and a plurality of vertices respectively representing the pixels within the input image, set a connection cost, which indicates how likely the plurality of vertices are to be connected to each other, based on the second evaluation value, and connect the vertices to each other based on the set connection cost, thereby extracting the specific region.

* * * * *